United States Patent
Ismail et al.

(10) Patent No.: US 12,324,665 B1
(45) Date of Patent: Jun. 10, 2025

(54) ATTENTION DEFICIT HYPERACTIVITY DISORDER ALERT DEVICE

(71) Applicant: KING FAISAL UNIVERSITY, Al-Ahsa (SA)

(72) Inventors: Abdelrahim Fathy Ismail, Al-Ahsa (SA); Remas Abdelrahim Fathy Ismail, Assiut (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/966,852

(22) Filed: Dec. 3, 2024

(51) Int. Cl.
  *G08B 21/00* (2006.01)
  *A61B 5/00* (2006.01)
  *A61B 5/16* (2006.01)

(52) U.S. Cl.
  CPC ............ *A61B 5/168* (2013.01); *A61B 5/7405* (2013.01); *A61B 5/7435* (2013.01); *A61B 5/7455* (2013.01); *A61B 5/749* (2013.01)

(58) Field of Classification Search
  CPC ..... A61B 5/168; A61B 5/7405; A61B 5/7435; A61B 5/7455; A61B 5/749
  See application file for complete search history.

(56) References Cited

U.S. PATENT DOCUMENTS

| | | | | |
|---|---|---|---|---|
| 7,008,378 | B2 * | 3/2006 | Dean | G16H 10/60 600/300 |
| 9,552,707 | B1 * | 1/2017 | Bala | G08B 6/00 |
| 2017/0303052 | A1 * | 10/2017 | Kakareka | G01S 3/86 |
| 2024/0185034 | A1 * | 6/2024 | Hatamizadeh | G06N 3/0464 |
| 2024/0343259 | A1 * | 10/2024 | Gupta | A61B 5/0077 |

FOREIGN PATENT DOCUMENTS

| CN | 113926188 A | * | 1/2022 |
|---|---|---|---|
| CN | 113988811 A | * | 1/2022 |

* cited by examiner

*Primary Examiner* — Toan N Pham
(74) *Attorney, Agent, or Firm* — Nath, Goldberg & Meyer; Joshua B. Goldberg

(57) ABSTRACT

The attention deficit hyperactivity disorder alert device includes a controller, non-transitory computer readable memory in communication with the controller, a user interface in communication with the controller, and a display in communication with the controller. The controller is configured to save a plurality of tasks in the non-transitory computer readable memory, assign priority levels to each of the tasks, and assign an alert frequency to each of the tasks. The controller is further configured to display each of the tasks to a user on the display, such that each of the tasks is displayed in a unique color representative of the priority level assigned thereto. The controller is further configured to deliver an alert for each of the tasks to the user, where the alert for each of the tasks is repeated at the alert frequency assigned thereto.

13 Claims, 3 Drawing Sheets

ATTENTION DEFICIT HYPERACTIVITY DISORDER ALERT DEVICE

BACKGROUND

Field

The disclosure of the present patent application relates to tools for assisting with attention deficit hyperactivity disorder (ADHD), and particularly to a device which issues regular reminders to a user to stay on task.

Description of Related Art

Children diagnosed with attention deficit hyperactivity disorder (ADHD) encounter challenges in sustaining attention and remaining focused while engaged in one or more tasks. Often, they overlook crucial details necessary for task completion and easily succumb to distractions during activities. Tasks requiring prolonged concentration are typically avoided, and distraction intensifies when tasked with sequential or parallel execution of two or three activities. Frequently, these children lose track of or forget to perform the second and third tasks midway. Additionally, organizational difficulties in handling tasks, assignments, and appointments result in misplaced items and delayed work.

Although people suffering from ADHD are taught various coping strategies, reminders to stay on task remain one of the most effective tools for allowing people with ADHD to complete tasks. Since teachers, parents, etc. are not always available to monitor children with ADHD and provide them with reminders, it would be desirable to provide a portable device which a child can carry and which would issue reminders. Thus, an attention deficit hyperactivity disorder alert device solving the aforementioned problems is desired.

SUMMARY

The attention deficit hyperactivity disorder alert device includes a controller, non-transitory computer readable memory in communication with the controller, a user interface in communication with the controller, and a display in communication with the controller. The controller is configured to save a plurality of tasks in the non-transitory computer readable memory, assign priority levels to each of the tasks, and assign an alert frequency to each of the tasks. The controller is further configured to display each of the tasks to a user on the display, such that each of the tasks is displayed in a unique color representative of the priority level assigned thereto. The controller is further configured to deliver an alert for each of the tasks to the user, where the alert for each of the tasks is repeated at the alert frequency assigned thereto.

The tasks may be entered by typing on a keyboard, such as that displayed on a touchscreen, for example, or may be entered by voice. The controller is further configured to convert spoken tasks into text using speech-to-text. 5. The alert for each of the tasks may be delivered as an audio alert through a speaker, a visual alert on the display, a haptic alert delivered by a haptic actuator, or a combination thereof.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
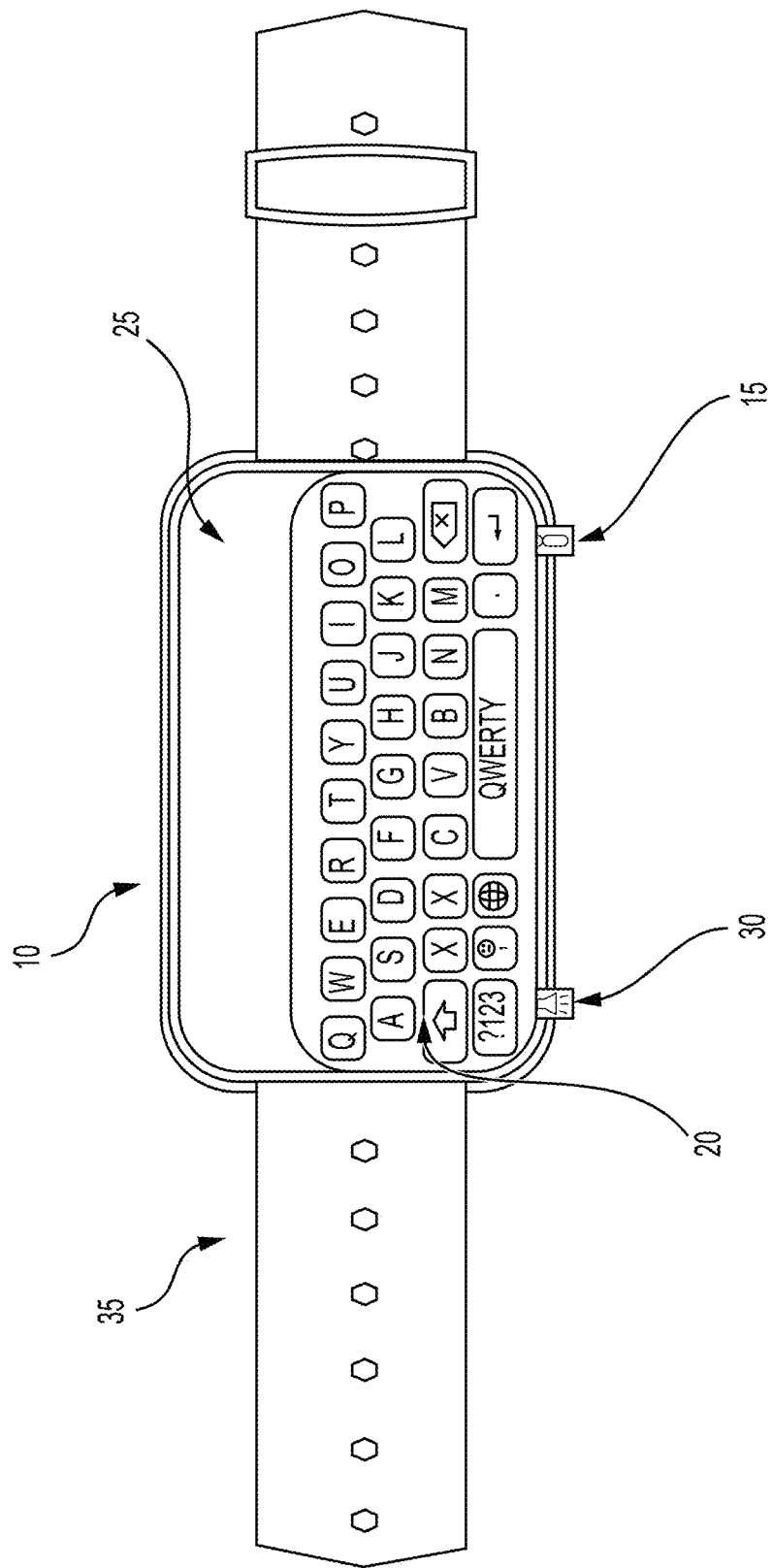
FIG. 1 is a front view of an attention deficit hyperactivity disorder (ADHD) alert device.

FIG. 1 is an illustration of an alert device 10 for supporting children with Attention Deficit Hyperactivity Disorder (ADHD). The alert device 10 includes a microphone 15, an audio recording system, and/or an electronic keyboard 20, enabling the input of task data, either through audio or written format. Integrated software determines the task order based on the level of importance of each task. Parents or the child individually input each task, associating a specific color within the software to signify the task's priority on the child's agenda. As a non-limiting example, red may be used for the first task, green may be used for the second task, and yellow may be used for the third task.

The alert device 10 further includes an audio alert bell, a small task display screen 25, and a built-in speaker 30. It should be understood that the display screen 25 and the keyboard 20 may be integrated together as a touchscreen. It should be further understood that the audio alert bell may be any suitable type of chime, alarm or other audio output played through the speaker 30.

A strap 35 is incorporated into the device 10 and is secured around the child's arm or wrist. A haptic actuator may also be incorporated into device 10, allowing device 10 to issue audio, vibration and/or light or visual alerts to remind the child to continue with the ongoing task, depending on the specified alert level in the software. As a non-limiting example, frequent reminders may be made every 5 minutes, moderate reminders may be made every 10 minutes, or gentle reminders may be made every 15 minutes. Audio alerts can be activated if the child is in an environment allowing sound, such as at home or on the street, while vibration or light/visual alerts can be used in noise-restricted settings, such as school, the library, or sound-prohibited areas.

The device 10 may, as a non-limiting example, restrict task entries to a maximum of three in order to prevent overwhelming distractions. In this example, should the child wish to add a fourth or fifth task, they can complete one of the three recorded tasks and replace it with a new one.

The integrated software allows customization of alert levels (e.g., frequent reminders every 5 minutes, moderate reminders every 10 minutes, or gentle reminders every 15 minutes) based on the child's preferences and needs. This device 10 may be used, as non-limiting examples, by children with ADHD in educational institutions, residences, and public spaces, thus aiding in the organization and execution of daily tasks.

Figure 3:
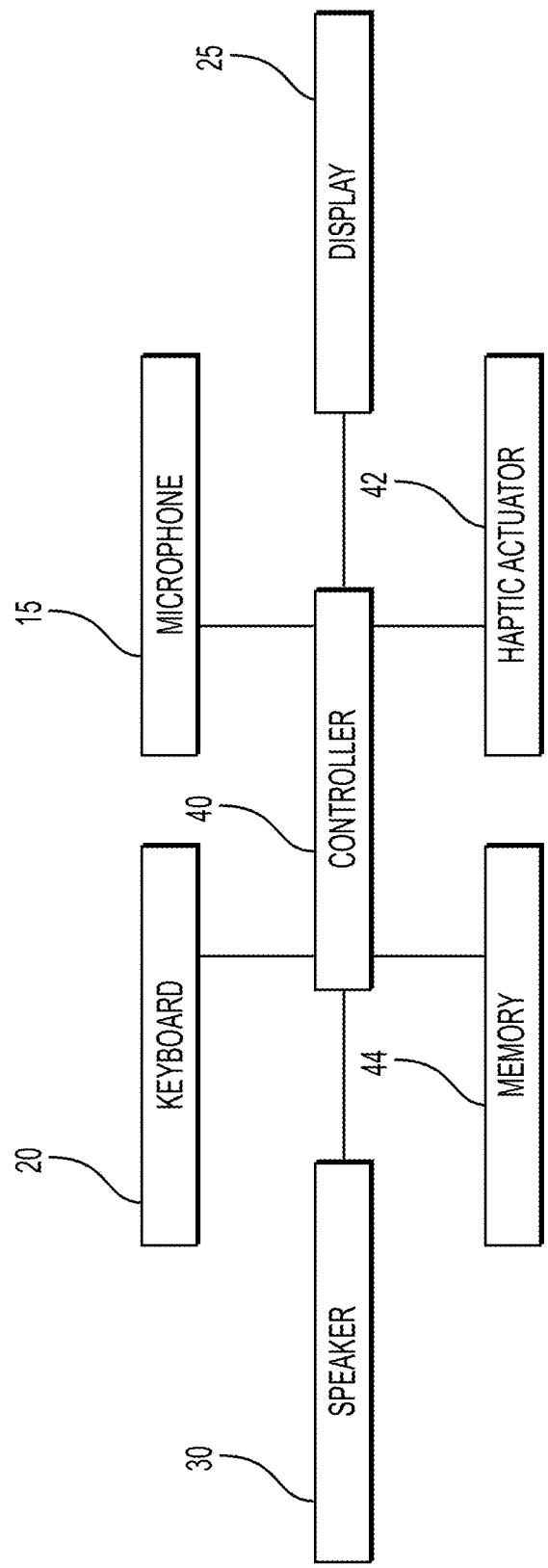
FIG. 3 is a block diagram illustrating system components of the ADHD alert device.

As shown in FIG. 3, microphone 15, keyboard 20, display 25, speaker 30 and haptic actuator 42 are each in communication with a controller 40, which runs the integrated software. Controller 40 may be any suitable type of controller, such as a processor, a programmable logic controller, control circuitry or the like. The software and saved data may be stored in memory 44, which may be any suitable type of non-transitory computer readable memory. The microphone 15, keyboard 20, display 25, speaker 30, haptic actuator 42, memory 44 and controller 40 may all be integrated into a smartwatch or the like, or may be used in a device specific to providing alerts to people with ADHD.

Figure 2:
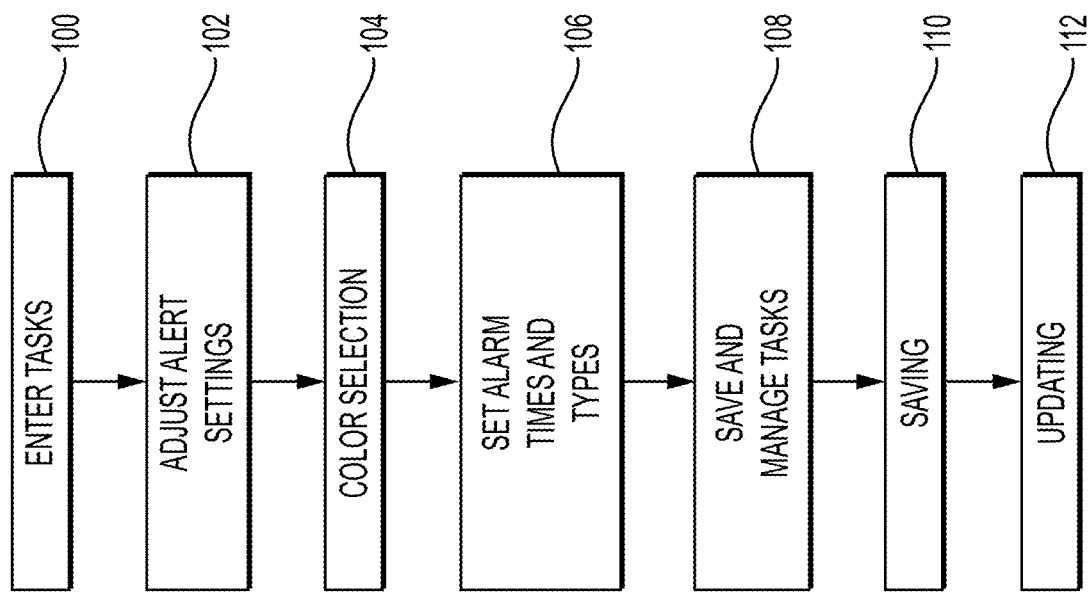
FIG. 2 a flow chart illustrating steps implemented by integrated software of the ADHD alert device.

FIG. 2 is a flow chart of one embodiment of the integrated software. The operating program is based on inputs, processes, and outputs in the form of alerts (sound, vibration, and/or light or visual signals) to prompt the child to complete the tasks previously entered into the device 10. At step 100, the tasks are entered, either by typing on keyboard 20 or by speaking into microphone 15. When using microphone 15, controller 40 may convert the spoken words into text using convention speech-to-text algorithms. The tasks may be entered by the child, a parent, a teacher or any other user. As a non-limiting example, the number of tasks may be limited to three at a time, since more than three tasks may confuse children with ADHD. Thus, a fourth task, for example, may only be entered after one of the three initial tasks has been completed. Non-limiting examples of common tasks include returning borrowed books to the library, completing homework, organizing a school bag, cleaning the child's room, exercising, doing homework, making a phone call, bathing, organizing a bookshelf, and scheduling or going to an appointment.

At step 102, the alter settings are entered. For example, at step 104, each task may be prioritized, with a particular color assigned to each task based on priority level. As a non-limiting example, an urgent task may be red, a task which may be performed later may be green, etc. The tasks displayed to the child on display 25 will appear written in the appropriate color. Each time a task is entered, a sub-interface may appear on the display 25 to define the colors that the user associates with the task. At step 104, the user may set the time between alerts (e.g., every 5, 10 or 15 minutes), as well as the type of alert (sound, vibration, light/visual, or a combination thereof). Further customization may be performed, such as, for example, customizing the sound of the audio alert (e.g., a bell sound, a specific tone, etc.), controlling the volume of the audio alert, adjusting the intensity of vibration generated by the haptic actuator 42, controlling the brightness of the display 25, activating or deactivating particular types of alerts, etc.

At step 108, the software enters a mode for saving and managing tasks. At step 110, following completion of entry of the tasks and setting the alert-related parameters, the task-related information is saved in memory 44. At step 112, tasks and priorities may be automatically updated. One a task is completed, a new task may be entered to replace the completed task. The tasks and priorities may be automatically updated after replacement, ensuring that the most important task retains its designated color.

It is to be understood that the attention deficit hyperactivity disorder (ADHD) alert device and method of using the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. An attention deficit hyperactivity disorder (ADHD) alert method, comprising:
 saving a maximum of three tasks in non-transitory computer readable memory;
 assigning priority levels to each of the three tasks;
 assigning an alert frequency to each of the three tasks;
 displaying each of the three tasks to an ADHD patient on a display wearable by the ADHD patient, wherein each of the three tasks is displayed in a unique color representative of the priority level assigned thereto; and
 delivering an alert for each of the three tasks to the ADHD patient, wherein the alert for each of the three tasks is repeated at the alert frequency assigned thereto.

2. The attention deficit hyperactivity disorder alert method as recited in claim 1, wherein each of the three tasks are entered by typing on a keyboard.

3. The attention deficit hyperactivity disorder alert method as recited in claim 1, wherein each of the three tasks are entered by voice.

4. The attention deficit hyperactivity disorder alert method as recited in claim 3, further comprising the step of converting each of the three tasks entered by voice into text.

5. The attention deficit hyperactivity disorder alert method as recited in claim 1, wherein the delivering of the alert for each of the three tasks comprises delivering an audio alert, a visual alert, a haptic alert, or a combination thereof.

6. An attention deficit hyperactivity disorder (ADHD) alert device, comprising:
 a controller;
 non-transitory computer readable memory in communication with the controller;
 a user interface in communication with the controller; and
 a display in communication with the controller and wearable by an ADHD patient,
 wherein the controller is configured to:
  save a a maximum of three tasks in the non-transitory computer readable memory;
  assign priority levels to each of the three tasks;
  assign an alert frequency to each of the three tasks;
  display each of the three tasks to the ADHD patient on the display, wherein each of the three tasks is displayed in a unique color representative of the priority level assigned thereto; and
  deliver an alert for each of the three tasks to the ADHD patient, wherein the alert for each of the three tasks is repeated at the alert frequency assigned thereto.

7. The attention deficit hyperactivity disorder alert device as recited in claim 6, wherein the interface comprises a keyboard.

8. The attention deficit hyperactivity disorder alert device as recited in claim 6, further comprising a microphone in communication with the controller.

9. The attention deficit hyperactivity disorder alert device as recited in claim 8, wherein the controller is further configured to convert voice input into text.

10. The attention deficit hyperactivity disorder alert device as recited in claim 6, further comprising a speaker in communication with the controller, wherein the alert for each of the three tasks is an audio alert.

11. The attention deficit hyperactivity disorder alert device as recited in claim 6, wherein the alert for each of the three tasks is a visual alert.

12. The attention deficit hyperactivity disorder alert device as recited in claim 6, further comprising a haptic actuator in communication with the controller, wherein the alert for each of the three tasks is a haptic alert.

13. The attention deficit hyperactivity disorder alert device as recited in claim 6, further comprising a wearable strap.

* * * * *